United States Patent [19]

Frank

[11] Patent Number: 4,877,915

[45] Date of Patent: * Oct. 31, 1989

[54] PROCESS FOR PREPARING POLYALKYL TETRAHYDRONAPHTHALENES

[75] Inventor: Walter C. Frank, Holland, Pa.

[73] Assignee: Union Camp Corporation, Wayne, N.J.

[*] Notice: The portion of the term of this patent subsequent to Oct. 31, 2006 has been disclaimed.

[21] Appl. No.: 303,364

[22] Filed: Jan. 27, 1989

[51] Int. Cl.⁴ .................. C07C 12/00; C07C 12/64; C07C 2/64
[52] U.S. Cl. .................. 585/411; 585/410; 585/452; 585/459
[58] Field of Search ............. 585/410, 411, 459, 452

[56] References Cited

U.S. PATENT DOCUMENTS

| | | | |
|---|---|---|---|
| 3,246,044 | 6/1963 | Wood et al. | 260/668 |
| 3,379,785 | 11/1965 | Kahn | 260/668 |
| 3,856,875 | 12/1974 | Wood et al. | 585/410 |
| 4,284,818 | 3/1979 | Sato et al. | 568/323 |
| 4,551,573 | 11/1985 | Cobb | 585/459 |
| 4,767,882 | 8/1986 | Suzukamo et al. | 560/100 |

FOREIGN PATENT DOCUMENTS

| | | |
|---|---|---|
| 2601670 | 2/1988 | France . |
| 57-40420 | 3/1982 | Japan . |
| 388527 | 3/1975 | U.S.S.R. . |

OTHER PUBLICATIONS

Boone et al., "The Acid-Catalyzed Alkylation and Cyclialkylation of the Cymenes with Isobutylene and Related Olefins", *J. Org. Chem.*, vol. 36, No. 15, pp. 2042-2048 (1971).
Coscia et al., "The Synthesis of 2,2-Ditolylpropane from α,p-dimethylstyrene", *J. Org. Chem.*, vol. 26, pp. 1398-1401 (1961).
Kondo et al., "Sulfonium Salts as Liquid-Liquid Phase-Transfer Catalysts", *Synthesis*, pp. 403-404 (1988).
Kennedy, *Carbocationic Polymerization*, p. 221 (Wiley-Interscience Publishers, 1982).

*Primary Examiner*—William R. Dixon, Jr.
*Assistant Examiner*—J. Saba
*Attorney, Agent, or Firm*—Edward J. Sites

[57] ABSTRACT

A process is disclosed for the production of polyalkyl tetrahydronaphthalenes wherein a cyclialkylation reaction between an olefinic compound of the general formula

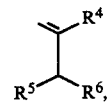

wherein $R^4$, $R^5$, and $R^6$ are substituents which do not interfere with a Friedel-Crafts-type reaction and $R^5$ and $R^6$ are other than H, and a substituted benzene compound is carried out in the presence of a hydride abstracting reagent, a Lewis acid, and, optionally, a phase transfer agent. In some embodiments, the subject process is specifically carried out in the absence of elemental iodine. The subject process produces the desired compounds in a surprisingly high yield, with a surprisingly high selectivity to the desired product, and at a relatively high rate of reaction, using better, more convenient or less expensive process methodology than many processes known heretofore.

48 Claims, No Drawings

4,877,915

PROCESS FOR PREPARING POLYALKYL TETRAHYDRONAPHTHALENES

BACKGROUND OF THE INVENTION

The present invention relates to an improved process for the production of polyalkyl tetrahydronaphthalenes, particularly, 1,1,3,4,4,6-hexamethyl-1,2,3,4-tetrahydronaphthalene, the latter compound referred to herein as "HMT".

HMT and other alkyl-substituted tetrahydronaphthalenes are of significant importance to the perfumery as well as other industries. By conventional acylation processes, HMT, for example, can be converted to 7-acetyl-1,1,3,4,4,6-hexamethyl-1,2,3,4-tetrahydronaphthalene, a well known musk perfume. Because of their clean musk fragrance and ability to retain that fragrance over long periods of time, these HMT derivatives are of great commercial value as synthetic musk perfume substitutes for the expensive, natural musk perfumes of the macrocyclic ketone series. Consequently, various synthetic methods have been proposed for the production of HMT, as well as other related intermediates of HMT useful in the perfumery or other industries.

For example, Cobb, U.S. Pat. No. 4,551,573 entitled "Alkylation of Aromatic Compounds," discloses a process for the alkylation of aromatic compounds with olefinic compounds in the presence of a catalyst consisting essentially of aluminum halide and elemental iodine. Examples of aromatic compounds described as suitable for use in the process include para-cymene, and olefinic compounds discussed include 2,3-dimethyl-2-butene, isobutylene and neohexene (3,3-dimethyl-1-butene). A mixture of olefinic compounds can also be employed, in which case it is noted that one of the olefins may function as a sacrificial agent. The products of the alkylation reaction described include indanes and HMT-type compounds.

Kahn, U.S. Pat. No. 3,379,785 entitled "Process for Preparing Polyalkyltetrahydronaphthalenes," relates to a process for preparing polyalkyl tetrahydronaphthalenes, and more specifically, a process for preparing HMT. The process involves the reaction of a substituted styrene and a 2,3-dimethylbutene, said reaction being carried out at elevated temperatures and in the presence of a cation exchange resin. The 2,3-dimethylbutene reactant employed is disclosed as comprising either 2,3-dimethyl-1-butene, 2,3-dimethyl-2-butene, or mixtures thereof. The preferably employed solvent comprises an aromatic hydrocarbon, such as, for example, benzene, toluene, ethylbenzene, or a xylene.

Japanese Patent Publication SHO 57-40420 discusses a method of making HMT characterized by reacting para-cymene and neohexene in the presence of anhydrous aluminum halide as catalyst. Suitable anhydrous aluminum halides are said to include aluminum chloride. The reaction is generally carried in a solvent, however, it is noted that it is possible to conduct the reaction without any additional solvent using excess para-cymene. Examples of suitable solvents are methylene chloride, ethylene chloride, chloroform and other inactive fatty hydrocarbon halides. Other solvents such as aromatic hydrocarbon halides, fatty hydrocarbons, aromatic hydrocarbons, etc., can be used, but it is noted that the use of such solvents generally lowers the yield of the desired end product.

Sato et al., U.S. Pat. No. 4,284,818 entitled "Process of Preparing Hexamethyltetrahydronaphthalenes," describes a process for producing HMT comprising reacting para-cymene with a 2,3-dimethyl butene using a catalytic amount of anhydrous aluminum halide in the presence of a secondary alkyl halide, tertiary alkyl halide, propargyl halide or allyl halide. It is noted that both the 2,3-dimethyl-1-butene and 2,3-dimethyl-2-butene can be employed as the 2,3-dimethyl butene reagent, however, 2,3-dimethyl-1-butene was said to yield better results. The reaction is generally carried out using a solvent, such solvents including aliphatic hydrocarbons, halogenated aromatic hydrocarbons, and halogenated aliphatic hydrocarbons.

Wood, U.S. Pat. No. 3,246,044 entitled "Process for Making 1,1,3,4,4,6-Hexamethyl-1,2,3,4-Tetrahydronaphthalene," discloses a process for preparing HMT which includes reacting an alpha,para-dimethylstyrene derivative such as dimethyl-para-tolyl-carbinyl halide, and neohexene in the presence of a catalyst such as aluminum chloride, aluminum bromide and ferric chloride, or other Friedel-Crafts catalysts, at low temperatures. Suitable solvents are listed as ethylene dichloride or carbon tetrachloride, or other inert chlorinated hydrocarbon solvents. It is noted that other solvents such as nitrobenzene and nitromethane, may be used, but the yield of desired product is indicated as generally being lower when such solvents are employed.

Wood et al., U.S. Pat. No. 3,856,875 entitled "Process for Producing 1,1,3,4,4,6-Hexamethyl-1,2,3,4-Tetrahydronaphthalene [sic] (HMT)," discusses a process for the preparation of HMT wherein an equivalent or excess amount of para-cymene is reacted with a substantially equal molar solution of neohexene and a tertiary alkyl halide in the presence of an effective amount of an anhydrous aluminum halide catalyst suspended in a reaction-compatible solvent. Although any tertiary alkyl halide can be employed in the disclosed process, tertiary butyl chloride, tertiary amyl chloride and 2,5-dichloro-2,5-dimethylhexane are noted as preferred. The process is described as having a solvent dependency, with the satisfactory solvents being ethylene dichloride, chloroform, methylene dichloride, 1,1,2,2-tetrachloroethane, 1,2dichloroethylene, 1,2,3-trichloropropane, 1,1,2-trichloroethane, monochlorobenzene, fluorobenzene, ortho-dichlorobenzene, and para-xylene. Numerous solvents are stated to be unsatisfactory for use in the disclosed process, such solvents including nitromethane, benzene, nitrobenzene, para-cymene, n-hexane, 1,2,2-trichloroethylene, carbon tetrachloride, 1,1,1-trichloroethane, carbon disulfide, 1,1,2,2,2-pentachloroethane, 1,2-dichloropropane, 1,1-dichloroethylene, and 1,1-dichloroethane. These unsatisfactory solvents are said to yield substantially poorer results.

Suzukamo et al., U.S. Pat. No. 4,767,882 entitled "Tetrahydronaphthalene Derivatives and Their Production," discloses a process for preparing a tetrahydronaphthalene derivative in an optically active state which comprises reacting a benzene compound and a pyrocine compound in the presence of a Lewis acid, or, alternatively, reacting the benzene with the pyrocine compound in the presence of an acid catalyst followed by treatment of the resultant product with the Lewis acid.

These prior art processes suffer from various drawbacks, including low conversion of reactants, poor selectivity to the desired products, sluggish reaction rates, unacceptably low temperature requirements, unsafe solvent systems, or oxygen sensitivity. New and/or better processes are needed. The present invention is directed to this important end.

SUMMARY OF THE INVENTION

The present invention provides a process for the production of polyalkyl tetrahydronaphthalenes wherein a cyclialkylation reaction between an olefinic compound of the general Formula

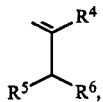

and a substituted benzene compound is carried out in the presence of a hydride abstracting reagent, a Lewis acid, and, optionally, a phase transfer agent. In some embodiments, the subject process is specifically carried out in the absence of elemental iodine. The subject process produces the desired compounds in a surprisingly high yield, with a surprisingly high selectivity to the desired product, and at a relatively high rate of reaction, using better, more convenient or less expensive process methodology than many processes known heretofore.

Specifically, the present invention pertains to a process for producing polyalkyl tetrahydronaphthalenes, such as those represented by the Formulas

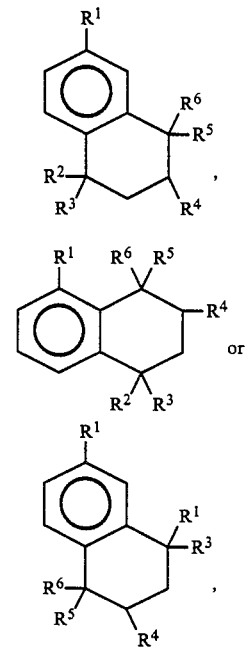

comprising contacting a partially substituted benzene compound, wherein said benzene compound is substituted with two or more substituents that do not substantially interefere with a Friedel-Crafts-type alkylation reaction said substituents including at least one secondary alkyl group having only one alpha-hydrogen, and wherein said benzene compound is unsubstituted in at least one position adjacent to said secondary alkyl group, such as those compounds of the Formulas

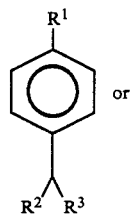

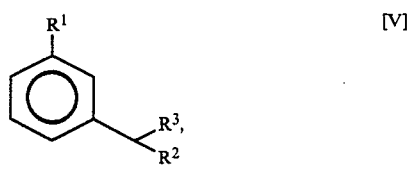

with an olefinic compound of the Formula

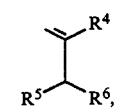

in the presence of a reagent of the Formula

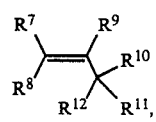

provided that said reagent has greater electron releasing properties than said olefinic compound VI, and further in the presence of a Lewis acid, wherein said process is carried out in the substantial absence of elemental iodine. In the above Formulas, $R^1$, $R^2$, $R^3$, $R^4$, $R^5$, $R^6$, $R^7$, $R^8$, $R^9$, $R^{10}$, $R^{11}$ and $R^{12}$ are, independently, substituents that do not substantially interfere with a Friedel-Crafts-type alkylation reaction, provided that (i) $R^1$, $R^2$, $R^3$, $R^5$ and $R^6$ are each other than H, (ii) no more than one of $R^7$, $R^8$ and $R^9$ are H, and (iii) no more than one of $R^{10}$, $R^{11}$ and $R^{12}$ are H. If desired, the process components may further include a phase transfer agent.

The present invention also pertains to a process for producing polyalkyl tetrahydronaphthalenes, such as those represented by the Formulas

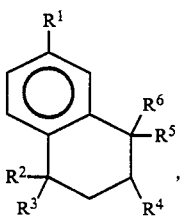

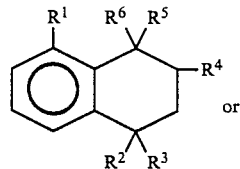

-continued

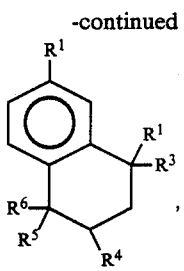
[III]

comprising contacting a partially substituted benzene compound, wherein said benzene compound is substituted with two or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, such as those compounds of the Formulas

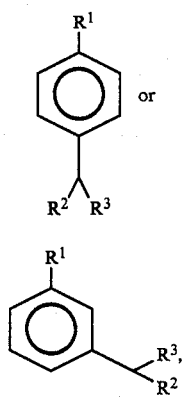
[IV]

or

[V]

with an olefinic compound of the Formula

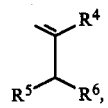
[VI]

in the presence of a reagent of the Formula

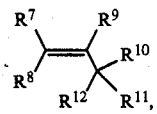
[VII]

provided that said reagent has greater electron releasing properties than said olefinic compound VI, and further in the presence of a Lewis acid and a phase transfer agent, wherein $R^1$, $R^2$, $R^3$, $R^4$, $R^5$, $R^6$, $R^7$, $R^8$, $R^9$, $R^{10}$, $R^{11}$ and $R^{12}$ are, independently, substituents that do not substantially interfere with a Friedel-Crafts-type alkylation reaction, provided that (i) $R^1$, $R^2$, $R^3$, $R^5$ and $R^6$ are each other than H, (ii) no more than one of $R^7$, $R^8$ and $R^9$ are H, and (iii) no more than one of $R^{10}$, $R^{11}$ and $R^{12}$ are H.

Using the foregoing process, one is able to produce a variety of alkyl-substituted tetrahydronaphthalene compounds for use as chemical intermediates and/or chemical products, particularly intermediates such as HMT, which is a compound of extreme importance to the fragrance industry.

DETAILED DESCRIPTION OF THE INVENTION

As noted above, the present invention pertains to a novel and particularly useful process for the production of polyalkyl tetrahydronaphthalenes including, but not limited to, those of Formulas I, II or III:

[I]

[II]

or

[III]

In the above Formulas, $R^1$, $R^2$, $R^3$, $R^4$, $R^5$ and $R^6$ are defined, independently, as substituents that do not substantially interfere with a Friedel-Crafts-type alkylation reaction, provided that $R^1$, $R^2$, $R^3$, $R^5$ and $R^6$ are each other than H. Such alkylation reactions and non-interfering substituents are discussed, for example, in George A. Olah, *Friedel-Crafts and Related Reactions*, Vols. 1 and 2 (Interscience Publishers, John Wiley and Sons, 1964) (hereinafter referred to as "*Friedel-Crafts Reactions*"), as well as in other journal and textbook references. The disclosures of *Friedel-Crafts Reactions* are incorporated herein by reference. Examples of suitable substituents include those wherein $R^4$ is H, or a $C_1$-$C_{30}$ straight chain, branched or cyclical alkyl, and $R^1$, $R^2$, $R^3$, $R^5$ and $R^6$, independently, are a $C_1$-$C_{30}$ straight chain, branched or cyclical alkyl. The alkyl is preferably a $C_1$-$C_{20}$, more preferably a $C_1$-$C_{10}$, and most preferably a $C_1$-$C_5$, alkyl. Preferably, the alkyl is a straight chain or branched alkyl. In a generally preferred embodiment, $R^1$, $R^2$, $R^3$, $R^4$, $R^5$ and $R^6$, independently, are a $C_1$-$C_5$ straight chain or branched alkyl.

In a most preferred embodiment, the polyalkyl tetrahydronaphthalenes are of the Formula I. The Formula I compounds are preferably:
1,1,3,4,4,6-hexamethyl-1,2,3,4-tetrahydronaphthalene (that is, HMT, a compound of Formula I wherein $R^1$, $R^2$, $R^3$, $R^4$, $R^5$ and $R^6$ are each methyl);
6-ethyl-1,1,3,4,4-pentamethyl-1,2,3,4-tetrahydronaphthalene (that is, a compound of Formula I wherein $R^1$ is ethyl, and $R^2$, $R^3$, $R^4$, $R^5$ and $R^6$ are each methyl);
6-tertiary-butyl-1,1,3,4,4-pentamethyl-1,2,3,4-tetrahydronaphthalene (that is, a compound of Formula I wherein $R^1$ is tertiary butyl, and $R^2$, $R^3$, $R^4$, $R^5$ and $R^6$ are each methyl); and 6-n-propyl-1,1,3,4,4-pentamethyl-1,2,3,4-tetrahydronaphthalene (that is, a compound of Formula I wherein $R^1$ is n-propyl, and $R^2$, $R^3$, $R^4$, $R^5$ and $R^6$ are each methyl).

The compounds of Formulas I, II and III are produced by contacting a partially substituted benzene compound, wherein said benzene compound is substituted with two or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, such substituted benzene compounds including, but not limited to, those of the Formulas IV or V

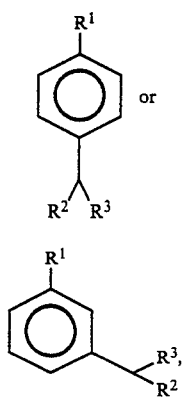

with an olefinic compound of the Formula VI

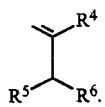

Reacting a benzene compound of Formula IV with an olefinic compound of Formula VI will yield the tetrahydronaphthalene compounds of Formula I. Alternatively, contacting a benzene compound of Formula V with an olefinic compound of Formula VI will yield the tetrahydronaphthalene compounds of Formulas II and III. The Formula I, II or III compounds may isomerize under the reaction conditions to also form compounds of one or more of the other Formula I, II or III compounds.

In the above Formulas IV, V and VI, $R^1$, $R^2$, $R^3$, $R^4$, $R^5$ and $R^6$ are defined, independently, as previously described, that is, as substituents that do not substantially interfere with a Friedel-Crafts-type alkylation reaction, provided that $R^1$, $R^2$, $R^3$, $R^5$ and $R^6$, are each other than H. Suitable substituents are discussed in various journal and textbook references, such as *Friedel-Crafts Reactions*. Suitable substituents include those wherein $R^4$ is H, or a $C_1$–$C_{30}$ straight chain, branched or cyclical alkyl, and $R^1$, $R^2$, $R^3$, $R^5$ and $R^6$, independently, are a $C_1$–$C_{30}$ straight chain, branched or cyclical alkyl. The alkyl is preferably a $C_1$–$C_{20}$, more preferably a $C_1$–$C_{10}$, and most preferably a $C_1$–$C_5$, alkyl. Preferably the alkyl is a straight chain or branched alkyl.

With respect to the benzene compounds of Formulas IV and V, a generally preferred embodiment includes those compounds wherein $R^1$, $R^2$ and $R^3$, independently, are a $C_1$–$C_5$ straight chain or branched alkyl. In a most preferred embodiment, the substituted benzene compounds are of Formula IV. The Formula IV compounds are preferably isopropyl toluene (that is, paracymene, a compound of Formula IV wherein $R^1$, $R^2$ and $R^3$ are each methyl), 1-ethyl-4-isopropylbenzene (that is, a compound of Formula IV wherein $R^1$ is ethyl, and $R^2$ and $R^3$ are each methyl), 1-n-propyl-4-isopropylbenzene (that is, a compound of Formula IV wherein $R^1$ is n-propyl, and $R^2$ and $R^3$ are each methyl), and 1-tertiary-butyl-4-isopropylbenzene (that is, a compound of Formula IV wherein $R^1$ is tertiary-butyl, and $R^2$ and $R^3$ are each methyl).

In a generally preferred embodiment, the olefinic compounds of Formula VI include those compounds wherein $R^4$ is H or a $C_1$–$C_5$ straight chain or branched alkyl, and $R^5$ and $R^6$, independently, are a $C_1$–$C_5$ straight chain or branched alkyl. A more preferable embodiment is wherein $R^4$ is methyl. Of the Formula VI compounds, 2,3-dimethyl-1-butene (a compound of Formula VI wherein $R^4$, $R^5$ and $R^6$ are each methyl), is most preferred. As those skilled in the art would recognize, as an alternative to adding the terminal olefinic compounds of Formula VI to the reaction mixture in carrying out the process of the invention, one may instead add the internal olefinic isomer of those compounds, that is, compounds of the Formula

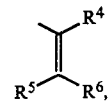

wherein $R^4$, $R^5$ and $R^6$ are as previously described. Such compounds are capable of rearranging by isomerization under the process conditions of the invention to form the Formula VI compounds believed to be required for polyalkyl tetrahydronaphthalene formation. A preferable internal olefinic isomer is 2,3-dimethyl-2-butene.

In accordance with the present invention, the compounds of Formulas IV or V are contacted with compounds of Formula VI in the presence of a reagent of the Formula

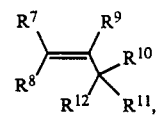

provided that said reagent has greater electron releasing properties than said olefinic compound, and further in the presence of a Lewis acid, and, optionally, a phase transfer agent.

In the above Formula VII, $R^7$, $R^8$, $R^9$, $R^{10}$, $R^{11}$ and $R^{12}$ are defined, as previously described, that is, as substituents that do not substantially interfere with a Friedel-Crafts-type alkylation reaction, provided that no more than one of $R^7$, $R^8$ and $R^9$ are H, and no more than one of $R^{10}$, $R^{11}$ and $R^{12}$ are H. Suitable substituents include those wherein $R^7$, $R^8$, $R^9$, $R^{10}$, $R^{11}$ and $R^{12}$ are, independently, H or a $C_1$–$C_{30}$ straight chain, branched or cyclical alkyl. The alkyl is preferably a $C_1$–$C_{20}$, more preferably a $C_1$–$C_{10}$ and most preferably a $C_1$–$C_5$ alkyl. Preferably the alkyl is a straight chain or branched alkyl. In a most preferred embodiment, the Formula VII compound is 2,4,4-trimethyl-2-pentene (that is, diisobutylene-2, a compound of Formula VII wherein $R^7$, $R^8$, $R^{10}$, $R^{11}$ and $R^{12}$ are methyl and $R^9$ is H). The particular reagents defined in Formula VII have been found to be surprisingly effective hydride abstractors. These compounds are capable of preferentially carrying out the hydride abstraction function, rather than participating in the alkylation step. This results in a process which has a smaller amount of side reactions occurring, and thus a higher selectivity to and yield of the desired end product.

As noted above, the Formula VII compounds employed in a process of the invention must have greater electron releasing properties than the olefinic compounds VI also utilized in that process. The comparative electron releasing properties of the Formula VI and VII compounds will be readily apparent to those skilled in the art. As will be recognized, for example, any of the Formula VII compounds wherein the $R^7$ through $R^{12}$ substituents are selected from H or alkyl, will have greater electron releasing properties than any of the Formula VI compounds wherein the $R^4$ through $R^6$ substituents are also selected from H or alkyl. Accordingly, it expected that the Formula VII compounds will function in the present process as the primary hydride abstracting agents, relieving the olefinic compounds VI of this task and enabling the Formula VI olefins to instead function as alkylating agents. In addition, as those skilled in the art will recognize, by utilizing the Formula VII compounds in accordance with the present process, one will be employing in a nonproductive reduction (hydride abstraction) step a more readily available, less expensive reagent VII, in lieu of the less readily available, more expensive alkyl halide compounds consumed in accordance with some prior art procedures. As a result, one is able to avoid by-product formation of hydrogen halides and accumulation of such compounds in the product stream, an undesirable result associated with some art processes. Moreover, the potential for corrosion problems within the reaction system concomitant with the formation of the hydrogen halides may be lessened, and the need for complex procedures for the separation of the desired tetralin products from the hydrogen halide by-products may be minimized.

Any Lewis acid, that is, any non-protonic compound capable of accepting an electron pair, is suitable for use in the present process. Exemplary Lewis acids include metal halides such as aluminum halides (including aluminum chloride, aluminum bromide, aluminum iodide, monofluorodichloroaluminum, monobromodichloroaluminum and monoiododichloroaluminum), alkyl metal halides and alkyl metals. Alkyl metals and alkyl metal halides suitable for use as Lewis acids in the present process are disclosed, for example, in Kennedy, Joseph P., *Carbocationic Polymerization*, p. 221 (Wiley-Interscience Publishers (1982)), the disclosures of which are incorporated herein by reference. In the process of the present invention, aluminum halides are preferred. Of the aluminum halides, aluminum chloride and aluminum bromide, particularly aluminum chloride, are most preferred.

In a preferable embodiment, the reaction is carried out in the presence of a phase transfer agent. Suitable phase transfer agents include onium salts such as ammonium, phosphonium and sulfonium salts. Other phase transfer agents suitable for use in the present process will be readily apparent to those skilled in the art, once having been made aware of the present disclosure.

Examples of ammonium phase transfer agents include quaternary ammonium halides such as methyltrioctylammonium chloride, methyltrinonylammonium chloride, methyltridecylammonium chloride, hexadecyltrihexylammonium bromide, ethyltrioctylammonium bromide, didodecyldimethylammonium chloride, tetraheptylammonium iodide, dioctadecyldimethylammonium chloride, tridectylbenzylammonium chloride, ditricosylmethylammonium chloride, and homologues thereof having chlorine, fluorine, bromine or iodine atoms substituted for the enumerated halide atom.

Exemplary phosphonium phase transfer agents include quaternary phosphonium halides such as tributyldecylphosphonium iodide, triphenyldecylphosphonium iodide, tributylhexadecylphosphonium iodide, and homologues thereof having chlorine, fluorine or bromine atoms substituted for the iodine atom.

Representative sulfonium phase transfer agents include ternary sulfonium halides such as lauryldimethylsulfonium iodide, lauryldiethylsulfonium iodide and tri(n-butyl)sulfonium iodide, and homologues thereof having chlorine, fluorine or bromine atoms substituted for the iodine atom.

These and other suitable phase transfer agents are described, for example, in Napier et al., U.S. Pat. No. 3,992,432 entitled "Phase Transfer Catalysis of Heterogeneous Reactions by Quaternary Salts," and in Kondo et al., *Synthesis*, pp. 403–404 (May 1988), the disclosures of which are incorporated herein by reference.

Preferable phase transfer agents are ammonium or sulfonium salts, particularly quaternary ammonium or ternary sulfonium halides. Most preferred are quaternary ammonium halides, particularly methyltrioctylammonium chloride (referred to herein as "MTOAc"), and a mixture of methyltrioctylammonium chloride and methyltridecylammonium chloride. The latter mixture is marketed under the trademark Adogen-464 ™, by Sherex Co., located in Dublin, Ohio.

In general, the molar proportions of the reagents employed in the present process can be varied over a relatively wide range. However, where phase transfer agents are employed in the process, it is important, for the best results, to maintain a ratio of less than one mole of phase transfer agent per mole of Lewis acid. Preferably, the molar ratio is about 0.8 to 1.0, more preferably 0.5 to 1.0, phase transfer agent to Lewis acid. It should be noted that some phase transfer agents sold commercially are sold in an impure form. Such impurities generally comprise water or an alcohol species. Water and alcohol, as well as other impurities, will react adversely with the Lewis acid, thereby lowering the amount of active Lewis acid available for the process of the present invention. Accordingly, where the phase transfer agent added contains such impurities, the amount of Lewis acid should be increased to account for these impurities. In such a situation the ratio of transfer agent to Lewis acid might be about 0.3 to 1.0. Such impure agent-containing mixtures are referred to herein as mixtures in an "impure form".

It is preferable to use a mixture of olefinic compound VI and hydride abstracting reagent VII wherein these components are present in a molar range of about 1.0 to about 5.0 moles of olefin VI per mole of reagent VII. More preferably, the olefin VI and reagent VII are present in nearly equimolar amounts, that is, about 1.0 mole of olefin VI per mole of hydride abstracting reagent VII.

Preferably, the substituted benzene compound is present in a range of about 0.5 to about 10 moles per mole of olefin VI. More preferably, the substituted benzene compound is present in a range of about 0.5 to about 5.0 per mole of olefin VI.

In a most preferred embodiment, each of the benzene compound, olefin VI, and the hydride abstracting reagent VII, are present nearly in equimolar amounts, that is, about 1.0 mole of benzene compound, to about 1.0 mole of olefin VI, to about 1.0 mole of hyride abstracting reagent VII.

The amount of Lewis acid utilized is preferably in the range of about 2% to about 10% by weight of the Lewis acid based on the combined weight of the substituted benzene, olefin VI, and hydride abstracting reagent VII.

As noted above, in certain embodiments, the present process must be conducted in the substantial absence of. elemental iodine ($I_2$). By "substantial absence", it is meant that only a deminimus amount of iodine (such as, for example, less than 1% by weight of $I_2$ based on the weight of the Lewis acid), if any, is present in the reaction medium. Preferably, in the embodiments which require a substantial absence $I_2$ iodine, the reaction medium is devoid of any elemental iodine.

The reaction is generally carried out using a solvent, although, if desired, substituted benzene, one of the starting materials, may be employed in large excess in lieu of an additional solvent. Representative of the halogenated solvents are aliphatic solvents methylene chloride, chloroform, carbon tetrachloride, ethylene chloride, ethylidene chloride, 1,1,1-trichloroethane, at 1,1,2-trichloroethane, 1,1,2,2-tetrachloroethane, 1,2-dichloroethylene, trichloroethylene, tetrachloroethylene, 1,2,3-trichloropropane, amyl chloride, and ethylene bromide, and the aromatic solvents monochlorobenzene, orthodichlorobenzene, bromobenzene and fluorobenzene. Exemplary of the unhalogenated solvents are the aliphatic solvents n-hexane, n-heptane and n-octane, the alicyclic solvent cyclohexane, and the aromatic solvents benzene, toluene, ethylbenzene and xylene. Preferred for reasons of yield, safety and/or process engineering are the unhalogenated aliphatic and unhalogenated alicyclic hydrocarbons. Other suitable halogenated and unhalogenated solvents are described, for example, in U.S. Pat. Nos. 4,284,818, 3,856,875 and 3,379,785, the disclosures of which are incorporated herein by reference.

The alkylation reaction of the invention can be carried out in any suitable vessel which provides efficient contacting between the Lewis acid and the other reactants. For simplicity, a stirred batch reactor can be employed. Although stirring is recommended to provide efficient contact between reactants, it has been found that with the addition of the phase transfer agent pursuant to one embodiment of the present invention, the Lewis acid is able to solubilize rather quickly, thereby obviating the need for the stringent stirring requirements of many of the art processes utilized to produce HMT. The reaction vessel used should be resistant to the possibly corrosive nature of the catalyst. Glass-lined vessels are suitable for this purpose as well as other vessel materials well known in the art.

The reagents of the present process may be added in any order, although where the process is carried out with a phase transfer agent, the preferred mode is to add the solvent, the Lewis acid and the phase transfer agent first, allow sufficient time for the Lewis acid to become substantially dissolved in the solvent, and then add the remaining reagents. Generally, 15 to 30 minutes are needed for the Lewis acid to become substantially dissolved in the solvent.

Ideally, the reaction is carried out at temperatures ranging from about −30° C. to about 50° C., preferably at temperatures ranging from about −10° C. to about 40° C., and most preferably at temperatures ranging from about 0° C. to about 30° C.

The pressure at which the reaction is carried out is not critical. If the reaction is carried out in a sealed vessel, autogenous pressure is acceptable, although higher or lower pressures, if desired, may be employed. The reaction can also be carried out at atmospheric pressure in an open reaction vessel, in which case the vessel is preferably equipped with a moisture trap to prevent significant exposure of Lewis acid to moisture. The reaction can take place in an oxygen atomsphere, or an inert atmosphere as in the presence of a gas such as nitrogen, argon and the like, the type of atmosphere also not being critical.

Reaction time is generally rather short and is often dictated by the kind of equipment employed. Sufficient time must be provided, however, for thorough contacting of the substituted benzene compound, the olefinic compound, the Lewis acid and the phase transfer agent. Generally the reaction proceeds to completion in about 1 to about 7 hours.

Product can be recovered by first quenching the reaction mixture in cold water or on crushed ice, preferably on ice, and then processing the mixture in the usual manner for Friedel-Crafts reactions to extract the desired alkyl-substituted tetrahydronaphthalene compounds. Suitable extraction protocol is described, for example, in *Friedel-Crafts Reactions*. Typically, following quenching and the resultant phase separation, the organic layer is washed an additional time with water to aid in removal of the Lewis acid. One or more additional washings can be carried out with dilute alkali solution to further aid Lewis acid removal. Pure product can then be recovered by subjecting the washed reaction mixture to reduced pressure fractional distillation.

The polyalkyl tetrahydronaphthalenes prepared in accordance with the processes of the invention, as hereinbefore indicated, may, for example, be acylated to obtain acylated polyalkyl tetrahydronaphthalenes having very fine, musk-like fragrances, a characteristic which renders them highly valuable for use in the perfumery industry. Such products, acylated or otherwise, may alternatively or additionally have utility in the pharmaceutical and/or agrochemical industries, either as intermediates or as end products, as generally discussed in French Patent Publication No. 2601670, and U.S. Pat. No. 4,551,573. The acylation process may be carried out using conventional methods, such as by reacting the polyalkyl tetrahydronaphthalene with an acyl halide or acid anhydride in the presence of an acid-acting catalyst. Suitable acylation methods are well known in the art and are disclosed, for example, in U.S. Pat. No. 4,284,818. Examples of acylated polyalkyl tetrahydronaphthalenes include 7-acetyl-1,1,3,4,4,6-hexamethyl-1,2,3,4-tetrahydronaphthalene, 7-acetyl-1,1,3,4,4-pentamethyl-6-ethyl-1,2,3,4-tetrahydronaphthalene, 7-acetyl-1,1,3,4,4,-pentamethyl-6-n-propyl-1,2,3,4-tetrahydronaphthalene, and 7-acetyl-1,1,3,4,4-pentamethyl-6-tertiary-butyl-1,2,3,4-tetrahydronaphthalene.

The present invention is further described in the following Examples. These Examples are not to be construed as limiting the scope of the appended Claims.

In each Example, the reaction flasks were equipped with a condenser, mechanical stirrer, addition funnel and thermocouple/temperature controller connected to an automatic laboratory jack. The flasks were cooled, when necessary, with a dry ice/isopropanol bath. The flask contents were continuously stirred throughout the reaction.

Results were analyzed on both polar and non-polar gas chromatography columns. All gas chromatography analyses were carried out on capillary columns using a weight percent internal standard method of analysis. Structure identifications wre assigned based on GCMS fragmentation patterns compared to standards. Examples 1-5 are examples of the processes of the present invention.

EXAMPLES

Example 1

A 100 ml, four-necked, round bottom flask was charged with methylene chloride (12.16 g) and anhydrous aluminum chloride (1.003 g) and cooled to about 16° C. A 60 ml addition funnel was charged with para-cymene (39.87 g), diisobutylene-2 (8.34 g), and 3-methyl-1-hexene (7.29 g), and connected to the flask. The funnel mixture was added over a period of about one hour, and the flask mixture stirred for 0.5 hours following addition while maintaining the temperature at about 16° C. The reaction was then quenched with deionized water (15 ml), and the organic phase separated and washed with, in order, 5% HCl, 10% $Na_2CO_3$ and 50% brine solution. The aqueous layers were individually extracted with ethyl ether, and the ether layers combined with the organic phase. The organics were then dried over $K_2CO_3$, filtered, and evaporated to yield a crude product (39.49 g) containing 23.82 weight % 1,1,4,6-tetramethyl-4-propyltetrahydronaphthalene (54.98% molar yield of the product based on the amount of 3-methyl-1-hexene charged).

Example 2

A 100 ml, four-necked, round bottom flask was charged with anhydrous aluminum chloride (1.006 g) and cyclohexene (7.15 g), and cooled to about 16° C. A 60 ml addition funnel was charged with para-cymene (39.87 g), 2,3-dimethyl-1-butene (6.25 g), and diisobutylene-2 (8.34 g) and connected to the flask. While maintaining a temperature of about 16° C., the funnel mixture was added to the flask over a period of about one hour and the flask mixture stirred an additional 30 minutes. The reaction was then quenched with deionized water (12 ml), and the organic phase separated and washed with, in order, 5% HCl, 10% $Na_2CO_3$, and 50% brine (solution). The aqueous layers were individually extracted with ethyl ether and the ether layers combined with the organic phase. The organics were then dried over $K_2CO_3$, filtered, and evaporated to yield a crude product (42.67 g) containing 24.51 weight % HMT (65.20% molar yield of HMT based on the amount of 2,3-dimethyl-1-butene charged).

Example 3

A 100 ml, four-necked, round bottom flask was charged with Adogen-464 TM (1.046 g), cyclohexane (7.15 g), and anhydrous aluminum chloride (1.000 g), and cooled to about 16° C. A 60 ml addition funnel was charged with para-cymene (39.87 g), 2,3-dimethyl-1-butene (6.25 g) and diisobutylene-2 (8.34 g). While maintaining a temperature of about 16° C., the funnel mixture was added to the flask over a period of about one hour, and the flask mixture stirred an additional 30 minutes. The reaction was then quenched with deionized water (12 ml), the layers separated, and the organic phase washed with, in order, 5% HCl, 10% $Na_2CO_3$ and 50% brine solution. The aqueous layers were individually extracted with ethyl ether, and the ether layers combined with the organic phase. The organics were then dried over $K_2CO_3$, filtered, and evaporated to yield a crude product (43.28 g) containing 23.85 weight % HMT (64.35% molar yield of HMT based on the amount of 2,3-dimethyl-1-butene charged).

Example 4

A 100 ml four-necked, round bottom flask was charged with methyltrioctylammonium chloride (2.73 g), anhydrous aluminum chloride (1.803 g) and cyclohexane (19.10 g), and cooled to about 20° C. A mixture containing para-cymene (25.13 g), 2,3-dimethyl-1-butene (7.63 g), and diisobutylene-2 (11.53 g), was added, with rapid stirring, to the flask over a period of about 3 hours. The reaction was immediately quenched with deionized water (15 ml) and worked up as previously described in Example 1 to give a crude product (31.16 g) containing 41.66 weight % HMT (66.16% molar yield of HMT based on the amount of 2,3-dimethyl-1-butene charged).

Example 5

A 100 ml, four-necked, round bottom flask was charged with methytrioctylammonium chloride (1.047 g), cyclohexane (7.15 g), and anhydrous aluminum chloride (1.001 g), and cooled to about 16° C. A mixture of paracymene (39.87 g), 2,3-dimethyl-1-butene (6.25 g) and diisobutylene-2 (8.34 g) was added to the flask from a 60 ml addition funnel over a period of about one hour while maintaining a flask temperature of about 16° C. The mixture was stirred for 30 minutes following addition, and the reaction quenched with deionized water (15 ml). The organic phase was worked-up as in Example 1 to yield a crude product (42.79 g) containing 25.16 weight % HMT (67.12 molar yield of HMT based on the amount of 2,3-dimethyl-1-butene charged).

Various modifications of the invention in addition to those shown and described herein will be apparent to those skilled in the art from the foregoing description. Such modifications are also intended to fall within the scope of the appended Claims.

What is claimed is:

1. A process for producing a polyalkyl tetrahydronaphthalene compound comprising contacting a partially substituted benzene compound, wherein said benzene compound is substituted with two or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, with an olefinic compound of the Formula

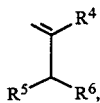

in the presence of a reagent of the Formula

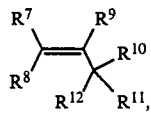

provided that said reagent has greater electron releasing properties than said olefinic compounds, and
a Lewis acid,
wherein
$R^4$, $R^5$, $R^6$, $R^7$, $R^8$, $R^9$, $R^{10}$, $R^{11}$ and $R^{12}$, independently, are substituents that do not substantially interfere with a Friedel-Crafts-type alkylation reaction, provided that
(i) $R^5$ and $R^6$ are each other than H,
(ii) no more than one of $R^7$, $R^8$ and $R^9$ are H, and
(iii) no more than one of $R^{10}$, $R^{11}$ and $R^{12}$ are H,
wherein said process is carried out in the substantial absence of elemental iodine.

2. A process for producing a polyalkyl tetrahydronaphthalene compound of the Formulas

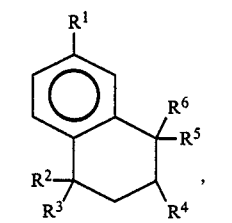

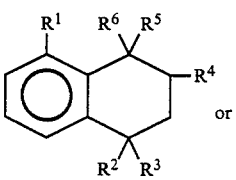

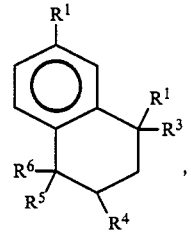

comprising contacting a partially substituted benzene compound of the Formulas

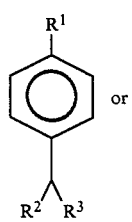

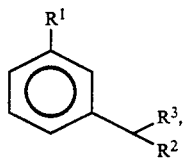

with an olefinic compound of the Formula

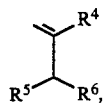

in the presence of a reagent of the Formula

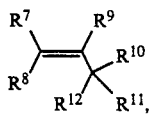

provided that said reagent has greater electron releasing properties than said olefinic compounds, and
a Lewis acid,
wherein
$R^1$, $R^2$, $R^3$, $R^4$, $R^5$, $R^6$, $R^7$, $R^8$, $R^9$, $R^{10}$, $R^{11}$ and $R^{12}$, independently, are substituents that do not substantially interfere with a Friedel-Crafts-type alkylation reaction, provided that
(i) $R^1$, $R^2$, $R^3$, $R^5$ and $R^6$ are each other than H,
(ii) no more than one of $R^7$, $R^8$ and $R^9$ are H, and
(iii) no more than one of $R^{10}$, $R^{11}$ and $R^{12}$ are H,
wherein said process is carried out in the substantial absence of elemental iodine.

3. A process of claim 2 wherein
$R^4$, $R^7$, $R^8$, $R^9$, $R^{10}$, $R^{11}$ and $R^{12}$, independently, are H, or a $C_1$–$C_{30}$ straight chain, branched or cyclical alkyl; and
$R^1$, $R^2$, $R^3$, $R^5$ and $R^6$, independently, are a $C_1$–$C_{30}$ straight chain, branched or cyclical.

4. A process of claim 3 wherein said alkyl is a $C_1$–$C_5$ alkyl.

5. A process of claim 3 wherein said alkyl is a straight chain or branched alkyl.

6. A process of claim 3 wherein said polyalkyl tetrahydronaphthalene compound is of the Formula.

7. A process of claim 6 wherein
$R^4$ is H or a $C_1$–$C_5$ straight chain or branched alkyl; and
$R^1$, $R^2$, $R^3$, $R^5$ and $R^6$, independently, are a $C_1$–$C_5$ straight chain or branched alkyl.

8. A process of claim 7 wherein
$R^1$, $R^2$, $R^3$, $R^4$, $R^5$ and $R^6$ are each methyl.

9. A process of claim 7 wherein
$R^1$ is ethyl; and
$R^2$, $R^3$, $R^4$, $R^5$ and $R^6$ are each methyl.

10. A process of claim 7 wherein
$R^1$ is n-propyl; and
$R^2$, $R^3$, $R^4$, $R^5$ and $R^6$ are each methyl.

11. A process of claim 7 wherein
$R^1$ is tertiary butyl; and
$R^2$, $R^3$, $R^4$, $R^5$ and $R^6$ are each methyl.

12. A process of claim 3 wherein said partially substituted benzene compound is of the Formula.

13. A process of claim 12 wherein

R$^1$, R$^2$ and R$^3$, independently, are a C$_1$-C$_5$ straight chain or branched alkyl.

14. A process of claim 13 wherein R$^1$, R$^2$ and R$^3$ are each methyl.

15. A process of claim 13 wherein R$^1$ is ethyl; and R$^2$ and R$^3$ are each methyl.

16. A process of claim 13 wherein R$^1$ is n-propyl; and R$^2$ and R$^3$ are each methyl.

17. A process of claim 13 wherein R$^1$ is tertiary-butyl; and R$^2$ and R$^3$ are each methyl.

18. A process of claim 3 wherein R$^4$ is H or a C$_1$-C$_5$ straight chain or branched alkyl; and R$^5$ and R$^6$, independently, are a C$_1$-C$_5$ straight chain or branched alkyl.

19. A process of claim 18 wherein R$^4$ is methyl.

20. A process of claim 18 wherein R$^4$, R$^5$ and R$^6$ are each methyl.

21. A process of claim 2 wherein said Lewis acid is selected from the group consisting of metal halides, alkyl metal halides and alkyl metals.

22. A process of claim 21 wherein said Lewis acid is metal halide which is an aluminum halide.

23. A process of claim 22 wherein said aluminum halide is aluminum chloride.

24. A process of claim 3 wherein R$^7$, R$^8$, R$^9$, R$^{10}$, R$^{11}$ and R$^{12}$, indepedently, are H or a C$_1$-C$_5$ straight chain, branched or cyclical alkyl.

25. A process of claim 24 wherein R$^7$, R$^8$, R$^{10}$, R$^{11}$ and R$^{12}$ are each methyl; and R$^9$ is H.

26. A process of claim 2 further comprising a solvent.

27. A process of claim 26 wherein said solvent is selected from the group consisting of unhalogenated aliphtic, unhalogenated alicyclic and unhalogenated aromatic hydrocarbon solvents.

28. A process of claim 27 wherein said unhalogenated alicyclic solvent is cyclohexane.

29. A process of claim 2 further comprising a phase transfer agent.

30. A process of claim 29 wherein said phase transfer agent is selected from the group consisting of ammonium, phosphonium and sulfonium salts.

31. A process of claim 30 wherein said ammonium salt is a quaternary ammonium halide.

32. A process of claim 31 wherein said quaternary ammonium halide is methyltrioctylammonium chloride.

33. A process of claim 31 wherein said quaternary ammonium halide is a mixture of methyltrioctylammonium chloride and methyltriecylammonium chloride.

34. A process of claim 29 wherein said phase transfer agent and said Lewis acid are present in a molar ratio of less than 1 to 1, phase transfer agent to Lewis acid.

35. A process of claim 34 wherein said phase transfer agent and said Lewis acid are present in a molar ratio of about 0.5 to 1.0.

36. A process of claim 34 wherein said phase transfer agent is in an impure form and said phase transfer agent and said Lewis acid are present in a molar ratio of about 0.3 to 1.

37. A process for producing a polyalkyl tetrahydronaphthalene compound comprising contacting a partially substituted benzene compound, wherein said benzene compound is substituted with two or more substituents that do not substantially interfere with a Friedel-Crafts-type alkylation reaction said substituents including at least one secondary alkyl group having only one alpha-hydrogen, and wherein said benzene compound is unsubstituted in at least one position adjacent to said secondary alkyl group, with an olefinic compound of the Formula

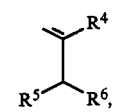
[VI]

in the present of a reagent of the Formula

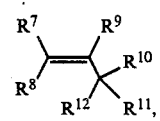
[VII]

provided that said reagent has greater electron releasing properties than said olefinic compounds,
   a Lewis acid, and
   a phase transfer agent,
wherein
   R$^1$, R$^2$, R$^3$, R$^4$, R$^5$, R$^6$, R$^7$, R$^8$, R$^9$, R$^{10}$, R$^{11}$ and R$^{12}$, independently, are substituents that do not substantially interfere with a Friedel-Crafts-type alkylation reaction, provided that
   (i) R$^1$, R$^2$, R$^3$, R$^5$ and R$^6$ are each other than H,
   (ii) no more than one of R$^7$, R$^8$, R$^9$ are H, and
   (iii) no more than one of R$^{10}$, R$^{11}$ and R$^{12}$ are H.

38. A process for producing a tetrahydronaphthalene compound of the Formulas

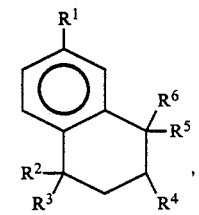
[I]

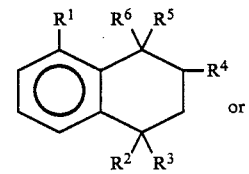
[II]

or

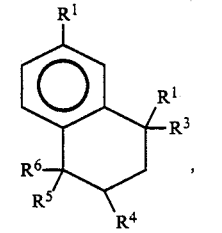
[III]

comprising contacting a partially substituted benzene compound of the Formulas

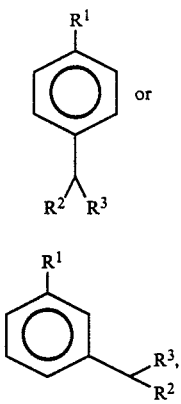

with an olefinic compound of the Formula

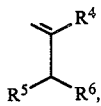

in the presence of a reagent of the Formula

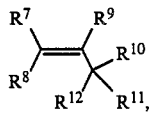

provided that said reagent has greater electron releasing properties than said olefinic compounds,
a Lewis acid, and
a phase transfer agent, wherein
$R^1$, $R^2$, $R^3$, $R^4$, $R^5$, $R^6$, $R^7$, $R^8$, $R^9$, $R^{10}$, $R^{11}$ and $R^{12}$, independently, are substituents that do not substantially interfere with a Friedel-Crafts-type alkylation reaction, provided that
(i) $R^1$, $R^2$, $R^3$, $R^5$ and $R^6$ are each other than H,
(ii) no more than one of $R^7$, $R^8$ and $R^9$ are H, and
(iii) no more than one of $R^{10}$, $R^{11}$ and $R^{12}$ are H, 39. A process of claim 38 wherein said phase transfer agent is selected from the group consisting of ammonium, phosphonium and sulfonium salts.

40. A process of claim 39 wherein said ammonium salt is a quaternary ammonium halide.

41. A process of claim 40 wherein said quaternary ammonium halide is methyltrioctylammonium chloride.

42. A process of claim 40 wherein said quaternary ammonium halide is a mixture of methyltrioctylammonium chloride and methyltridecylammonium chloride.

43. A process of claim 38 wherein said phase transfer agent and said Lewis acid are present in a molar ratio of less than 1 to 1, phase transfer agent to Lewis acid.

44. A process of claim 43 wherein said phase transfer agent and said Lewis acid are present in a molar ratio of about 0.5 to 1.0.

45. A process of claim 43 wherein said phase transfer agent is in an impure form and said phase transfer agent and said Lewis acid are present in a molar ratio of about 0.3 to 1.

46. A process of claim 38 further comprising a solvent.

47. A process of claim 46 wherein said solvent is selected from the group consisting of unhalogenated aliphatic, unhalogenated alicyclic and unhalogenated aromatic hydrocarbon solvents.

48. A process of claim 47 wherein said unhalogenated alicyclic solvent is cyclohexane.

* * * * *